United States Patent [19]

Szeles

[11] Patent Number: 4,677,531
[45] Date of Patent: Jun. 30, 1987

[54] INSPECTION ILLUMINATION DEVICE

[75] Inventor: Donald M. Szeles, Ann Arbor, Mich.

[73] Assignee: Applied Intelligent Systems, Inc., Ann Arbor, Mich.

[21] Appl. No.: 824,895

[22] Filed: Jan. 31, 1986

[51] Int. Cl.⁴ .............................................. F21V 8/00
[52] U.S. Cl. ...................... 362/32; 362/293; 350/96.26
[58] Field of Search ............ 362/19, 32, 268, 293, 362/804, 331; 350/96.18, 96.27, 96.26, 96.24; 358/901

[56] References Cited

U.S. PATENT DOCUMENTS

| | | | |
|---|---|---|---|
| 2,184,138 | 12/1939 | Corey | 362/19 |
| 3,327,712 | 6/1967 | Kaufman et al. | 350/96.26 |
| 3,596,083 | 7/1971 | Lovering | 362/32 |
| 3,740,115 | 6/1973 | Cole | 350/96.26 |
| 3,930,149 | 12/1975 | French | 362/293 |
| 4,483,585 | 11/1984 | Takami | 350/96.18 |

Primary Examiner—Charles J. Myhre
Assistant Examiner—D. M. Cox
Attorney, Agent, or Firm—Cullen, Sloman, Cantor, Grauer, Scott & Rutherford

[57] ABSTRACT

A device useful for illuminating parts to be inspected includes an illumination device employing a plurality of bundles of optical fibers coupled with a light source. The device includes a housing having an optical lens in one end which has an outer surface that is convex about a single axis. A clamp assembly mounts the bundles on the opposite end of the housing, with the ends of the bundles extending through a rectangular opening in an end wall of the housing. An aperture plate between the lens and the ends of the bundles masks light from the bundles so that all of the light passing through the aperture plate falls on the lens, thereby partially collimating the light impinging on the inner face of the lens.

17 Claims, 6 Drawing Figures

INSPECTION ILLUMINATION DEVICE

TECHNICAL FIELD

The present invention broadly relates to illumination systems, and deals more particularly with an illumination device employing bundles of optical fibers, which is especially useful in illuminating parts or surface features for inspection.

BACKGROUND ART

Numerous types of inspection processes require specialized sources of light to provide proper illumination of a part or features to be inspected. One typical application of specialized light sources for inspection processes involves the inspection of printed circuit boards at an intermediate step in their fabrication. Electrical components have pins or electrical leads which are inserted through holes in the board by automated equipment. After insertion, the leads may be crimped by automated machinery and are thereafter soldered to the printed circuit on the board. For any of various reasons, the leads may not be properly inserted through the holes in the board, and it is therefore necessary to inspect the leads after the insertion process to assure that the leads properly extend through the board and/or are properly crimped. Various systems, typically employing video cameras are used to automatically inspect the leads after they have been inserted. In order to properly view the leads with "artificial" vision system, it is necessary to illuminate the leads in a manner such that light is reflected from the leads to the camera.

Complicating the goal of proper illumination of printed circuit boards, and other objects having similar features, is the fact that the boards are of different sizes, may be held in various kinds of attitudes by automated inspection equipment and have different types of leads crimped in various manners at different attitudes using different techniques. It is, therefore, important to provide an illumination device which illuminates as wide of an area as possible while, at the same time, is of relatively low cost and easily set up to accommodate changing product inspection applications.

In inspection applications of the type described above, it is also necessary to achieve an illumination condition in which the electrical leads are illuminated in relatively high contrast relative to the board. In the past, others have employed bundles of optical fibers illuminating a spherical lens to provide the necessary illumination. This prior approach was relatively position-sensitive in terms of its ability to thoroughly illuminate given surface features. The problem of position sensitivity can be overcome, in part, by employing a larger light source, but this alternative is undesirable because of its expense.

There is, therefore, a need in the art for an illumination device which employs a relatively modest size light source which can easily and quickly be set up to accommodate varying inspection illumination requirements, while, at the same time, is not sensitive to position and provides a relatively constant intensity of light over a substantial distance from the light source.

SUMMARY OF THE INVENTION

In accordance with the present invention, an illumination device is provided comprising a housing and a plurality of elongate bundles of optical fibers connecting the housing with a source of light. The bundles are mounted on the housing by a clamping assembly which clamps the bundles in a linear array at a point spaced from the ends of the bundles. The ends of the bundles are received within a rectangular opening in one end wall of the housing and are arranged in rows so as to provide substantially uniform illumination over the entire cross-sectional area of the opening.

The opposite end of the housing is provided with a rectangular lens which is outwardly curved or convex about a single axis. An aperture plate within the housing between the ends of the optical fibers and the lens is provided to mask the dispersing light from the fibers such that all of the light passing through the aperture impinges on the inner, flat face of the lens. The aperture plate functions to partially collimate light delivered through the lens and to reduce the amount of scattered and reflected light within the housing. The light output by the device is a substantially rectangular beam of uniform intensity over its entire area and is substantially focused in one dimension over a substantial depth.

BRIEF DESCRIPTION OF THE DRAWINGS

In the drawings, which form an integral part of the specification and are to be read in conjunction therewith, and in which like components are designated by identical numerals in the various views.

DESCRIPTION OF THE PREFERRED EMBODIMENTS

Figure 1:
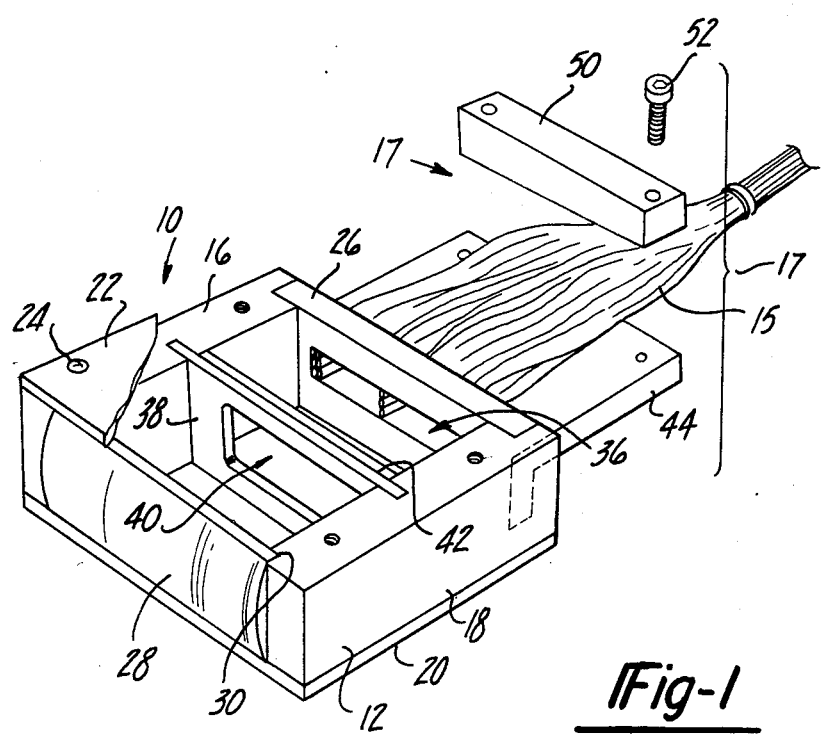
FIG. 1 is a partially exploded, perspective view of the illumination device which forms the preferred embodiment of the present invention, parts of the cover being broken away in section to reveal the interior of the housing and only a portion of the ends of the bundles being depicted.
Figure 2:
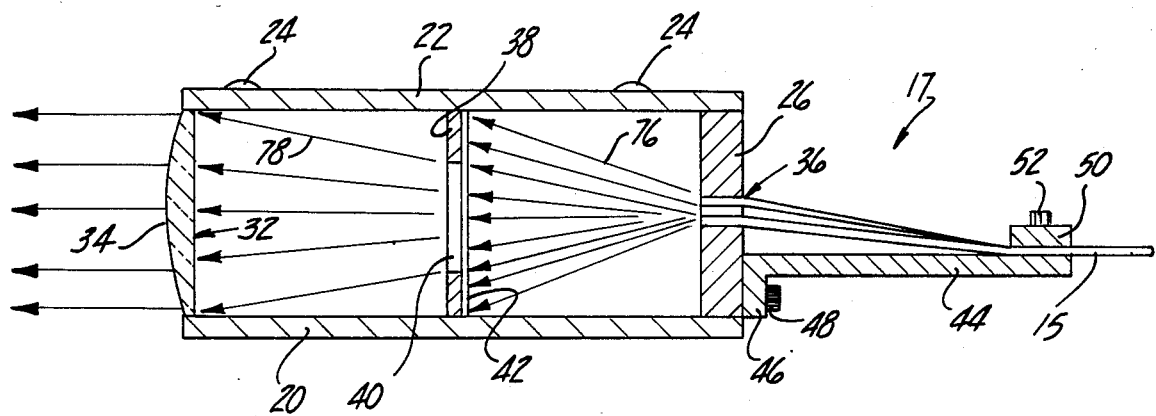
FIG. 2 is a longitudinal sectional view of the device of FIG. 1.

Referring first to FIGS. 1 and 2, the present invention broadly relates to an illumination device, generally indicated by the numeral 10, which is advantageously employed in illuminating parts or surface features to be inspected. The device 10 broadly includes a substantially rectangular housing 12 which is connected with a source of light (not shown) by means of bundles 15 of optical fibers which act as conduits of the light. The housing 12 includes a pair of spaced apart side walls 16, 18, an end wall 26 and top and bottom walls defined by a pair of plates 22, 20, respectively, which are secured to the end walls 16, 18 by means of screws 24. The aforementioned components of the housing 10 may be constructed of any suitable material, such as metal, and the interior portions thereof within the housing 10 are preferably coated with a black, non-reflective coating.

The end wall 26 is provided with a rectangular opening 36 therein for receiving the outer ends of the individual bundles 15 of optical fibers. Each bundle 15 may include, for example, 64 optical fibers, each of which is 0.010 mm in diameter. The bundles 15 of optical fibers are mounted on the housing 12 by means of a clamping assembly 17. The clamping assembly 17 includes a support plate 44 mounted on the end wall 26 by means of a flange 46 and screws 48. The support plate 44 extends rearward of the end wall 26. A clamping bar 50 is secured to the outer end of the support plate 44 by means of screws 52. At the outer end of the support plate 44, the individual bundles 15 are arranged in a single layer or row defining a linear array and are clamped to the plate 44 by means of the clamping bar 50. Between the outer end of the support plate 44 and the end wall 26, the bundles fan out so that the outer ends of each bundle are arranged in three rows or layers within the opening 36, there being approximately the same number of bundles in each of these rows so as to be uniformly distributed across the length and height of the opening 36. As best seen in FIG. 2, the outer ends of the bundles 15 extend into the end wall 26 and are essentially coplanar with its inner surface.

The end of the housing 12 opposite end wall 26 is provided with an optical lens 28 which is received in notches 30 of side walls 16 and 18. The optical lens 28 is preferably formed of a high quality glass and extends across the entire width of the opening defined between the side walls 16 and 18. The optical lens 28 has an essentially flat inner surface 32 and an outer surface 34 which is convex about a single axis extending along the longitudinal axis of the optical lens 28.

The distance between the end wall 26 and the lens 28 is preferably slightly greater than the focal length of the lens 28. Approximately equidistant between the end wall 26 and lens 28, there is provided an apertured plate 38 having a substantially rectangular aperture 40 therein. The plate 38 is received within slots in the side walls 16 and 18, and extends parallel to the end wall 26 and lens 28. A linear polarizer 42 is mounted immediately in back of the apertured plate 38 such that all light passing through the aperture 40 also passes through the polarizer 42. In lieu of the polarizer 42, any other suitable medium may be provided to change the wave length of the light passing through the aperture 40. Placing the aperture 40 approximately mid-way between the end wall 26 and the lens 28 has the advantage of reducing the effect that irregularities in the polarizer 42 have on the light emanating from the device 10.

The substantial length of the bundles 15 between the clamping block 50 and the end wall 26 assists in eliminating the angular sensitivity of illumination provided by the device 10. Light emanating from the ends of the optical bundles 15 is broadly dispersed at 76. The rectangular opening 40 in the apertured plate 38 is sized such that all of the polarized light passing through the aperture 40 at 78 falls on the flat face 32 of the lens 28. The masking action of the apertured plate 38 assists in partially collimating the light impinging on the lens 28 and reduces the amount of scattered or reflected light within the housing 12.

Figure 5:
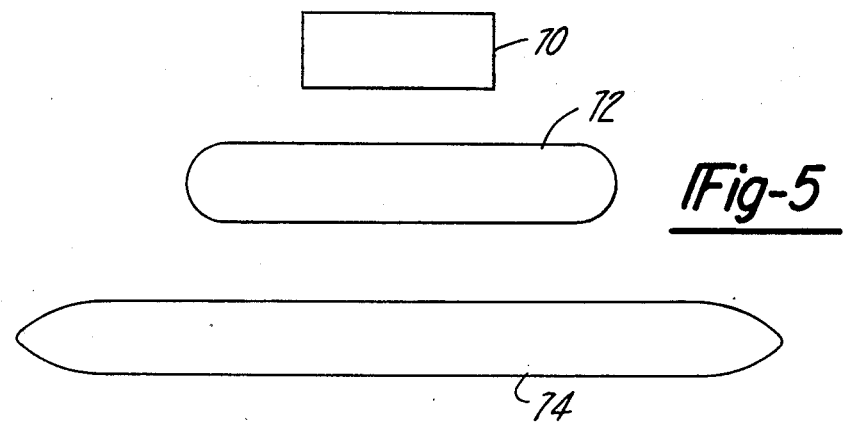
FIG. 5 is a view of the pattern of light delivered by the device of FIG. 1 at successively greater distances from the device.

The widths of the opening 36, aperture 40 and the lens 28 are preferably as wide as possible relative to the object or features that are to be illuminated. The lens 28 posseses a finite focus and the resulting pattern of illumination is such that one dimension of such pattern, i.e., the height, is maintained essentially constant over a wide depth of field. This is shown in FIG. 5 wherein the pattern of light provided at the focal distance is indicated at 70, and the patterns at successively greater distances, indicated respectively at 72 and 74, possess essentially the same height but diverge in width.

Figure 3:
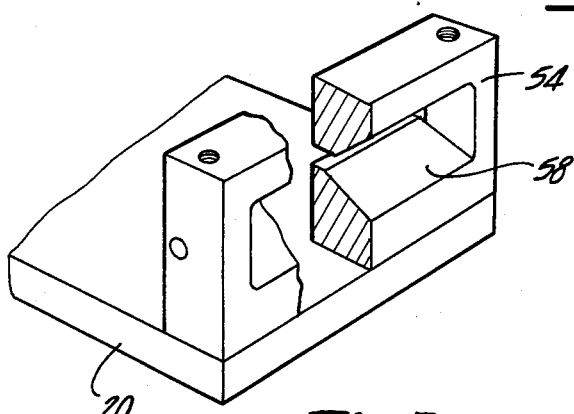
FIG. 3 is an alternate form of the end wall.
Figure 4:
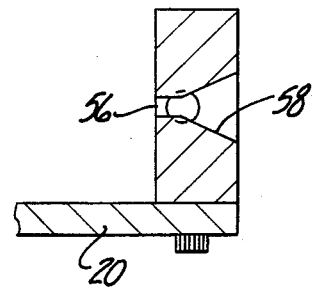
FIG. 4 is a cross-sectional view of the end wall shown in FIG. 3.

As shown in FIGS. 3 and 4, the end wall 26 may possess an opening 56 which communicates with outwardly tapering surfaces 58 which aid in inserting the ends of the bundles 15 into the opening 56.

Figure 6:
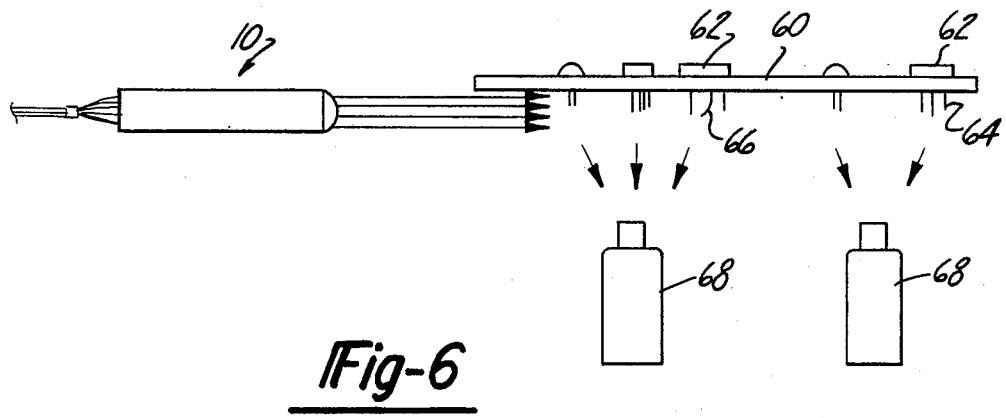
FIG. 6 is an elevational view of an arrangement for inspecting a printed circuit board using the inspection device of FIG. 1.

One typical use of the illuminating device 10 is depicted in FIG. 6, wherein a printed circuit board 60 has components 62 inserted therein and the electrical pins or leads 64 of the components 62 are being visually inspected by a pair of television cameras 68. One or more of the leads 64 may be missing or may be bent, as indicated at 66, and these are features that must be detected during the inspection process. The illumination device provides a rectangular pattern of light which is shone parallel to the bottom of the board 60 so as to graze the outer extremity of each of the leads 64. Light impinging on the outer extremities of the leads 64 is reflected perpendicularly to the camera 68. This illumination arrangement provides a relatively high contrast so that missing or crimped leads may be detected. The pattern of illumination provided by the illumination device has a relatively constant intensity across its height, and across the entire depth of the board 60.

It is recognized that those skilled in the art may make various modifications or additions to the preferred embodiment chosen to illustrate the invention without departing from the spirit and scope of the present contribution to the art. Accordingly, it is to be understood that the protection sought and to be afforded hereby should be deemed to extent to the subject matter claimed and all equivalents thereof fairly within the scope of the invention.

What is claimed is:

1. An illumination device, comprising:
    a housing;
    a plurality of elongate bundles of optical fibers adapted to be coupled with a source of light;
    means on said housing for clamping said bundles on said housing intermediate the ends of said bundles;
    a wall on one end of said housing having a substantially rectangular opening therein, the ends of said bundles being disposed substantially within said opening and directing light transmitted by said fibers into said housing and toward the opposite end of said housing;
    an optical lens on said opposite end of said housing through which light may emanate from said housing toward an object to be illuminated, said optical lens being substantially rectangular in shape and including a substantially flat inner surface and an outer surface which is convex about a single axis which is parallel to said inner surface; and
    a masking plate within said housing and between said wall and said optical lens, said masking plate having a substantially rectangular aperture therein, said aperture being sized such that all of the light from said optical fibers which passes through said aperture falls on said optical element.

2. The illumination device of claim 1, wherein said clamping means includes:
    an elongate support having one end thereof secured to said housing, the opposite end of said support being spaced from said one end of said housing;
    an elongate clamping member extending transverse to said bundles, said bundles being clamped between said clamping member and the opposite end of said support; and means for drawing said clamping member toward said support and into clamping engagement with said bundles.

3. The illumination device of claim 2 wherein said support includes a plate secured to said wall on said housing.

4. The illumination device of claim 1, wherein intermediate portions of said bundles are held by said clamping means in side by side relationship to each other to define a single row of said bundles.

5. The illumination device of claim 1, wherein said masking plate is substantially equidistant from said optical lens and said wall.

6. The illumination device of claim 1, including a linear polarizing element in said housing for polarizing light passing from said fibers to said optical lens.

7. The illumination device of claim 1, wherein said optical element defines an end wall of said housing.

8. The illumination device of claim 1, wherein:
said bundles are held in a side by side linear array by said clamping means, and
said bundles fan out from said clamping means toward said wall, the ends of said bundles being arranged in superimposed rows.

9. The illumination device of claim 1, wherein said opening in said wall is tapered in the direction of the axes of the bundles.

10. An illumination device for use with a plurality of elongate bundles of optical fibers, said bundles being adapted to be coupled with a source of light, comprising:
a housing having first and second opposing end walls, said first end wall having an opening therein, the ends of said bundles extending through said opening and directing light into said housing toward said second end wall;
an optical lens on said housing and spaced from the ends of said bundles for focusing light from said bundles onto an object to be illuminated, said opening in said first end wall and said optical lens each being substantially rectangular; and
means within said housing and disposed intermediate said first end wall and said lens for masking the light passing from the ends of said bundles to said optical lens, the location and size of said masking means being selected so that essentially all of the light passing through said masking means from said bundles falls directly on said optical lens without reflection from any surfaces within said housing.

11. The illumination device of claim 10, wherein said masking means includes a plate extending parallel to and intermediate said end walls, said plate having a substantially rectangular opening therein.

12. The illumination device of claim 10, wherein said optical lens includes a substantially flat inner surface facing said plate and an outer surface which is convex about a single axis which is parallel to said inner surface.

13. The illumination device of claim 12, wherein said optical lens and said masking means are shaped and dimensioned so that the cross-sectional shape of the beam of focused light emanating from said device is substantially rectangular and wherein said beam has a width measured perpendicularly to said single axis which remains substantially constant along its length.

14. The illumination device of claim 10, wherein said lens defines said second wall, and said first and second walls are spaced apart an amount which is at least as great as the focal length of said optical element.

15. The illumination device of claim 10, including means for mounting said bundles on said housing, said mounting means including means for clamping said bundles at a section along the length of said bundles spaced from said ends.

16. The illumination device of claim 15, wherein said clamping means includes a plate secured to said housing, and means including a clamping member for drawing said bundles against said plate.

17. The illumination device of claim 10, wherein said opening in said first end wall is tapered along the axis of said bundles.

* * * * *